United States Patent [19]

Peterson et al.

[11] 4,452,253

[45] Jun. 5, 1984

[54] COLLECTION BAG

[75] Inventors: James J. Peterson, Elgin; Glenn N. Taylor, Cary, both of Ill.

[73] Assignee: The Kendall Company, Boston, Mass.

[21] Appl. No.: 314,932

[22] Filed: Oct. 26, 1981

Related U.S. Application Data

[60] Division of Ser. No. 137,225, Apr. 4, 1980, Pat. No. 4,313,447, which is a continuation-in-part of Ser. No. 004,972, Jan. 22, 1979, abandoned, which is a continuation of Ser. No. 791,658, Apr. 28, 1977, abandoned.

[51] Int. Cl.³ .............................................. A61F 5/44
[52] U.S. Cl. ..................................... 128/766; 604/326
[58] Field of Search ............... 128/275, 766, 272, 760; 220/359, 270; 604/488

[56] References Cited

U.S. PATENT DOCUMENTS

| | | | |
|---|---|---|---|
| 2,102,440 | 12/1937 | Sebell | 220/276 X |
| 3,270,790 | 9/1966 | Clark | 128/275 X |
| 3,282,477 | 11/1966 | Henchert | 220/258 X |
| 3,343,542 | 9/1967 | Ericson | 128/275 |
| 3,394,831 | 7/1968 | Bathish et al. | 128/272 |
| 3,954,105 | 5/1976 | Nordley et al. | 128/275 |
| 4,015,605 | 4/1977 | McWhorter | 128/294 |

Primary Examiner—George F. Lesmes
Assistant Examiner—Nancy A. B. Swisher
Attorney, Agent, or Firm—Powell L. Sprunger

[57] ABSTRACT

A collection bag for receiving and collecting body fluids comprising, a receptacle having a pair of opposed walls defining a chamber, with one of the walls having an opening communicating with the chamber, and a connector having a cavity to receive the body fluids. The connector is attached to the one wall over the opening with the connector cavity communicating with the receptacle chamber to permit passage of fluids from the connector into the chamber for collection therein, and the connector may be ruptured from the one wall after use of the bag to permit access to the collected fluids through the opening.

1 Claim, 6 Drawing Figures

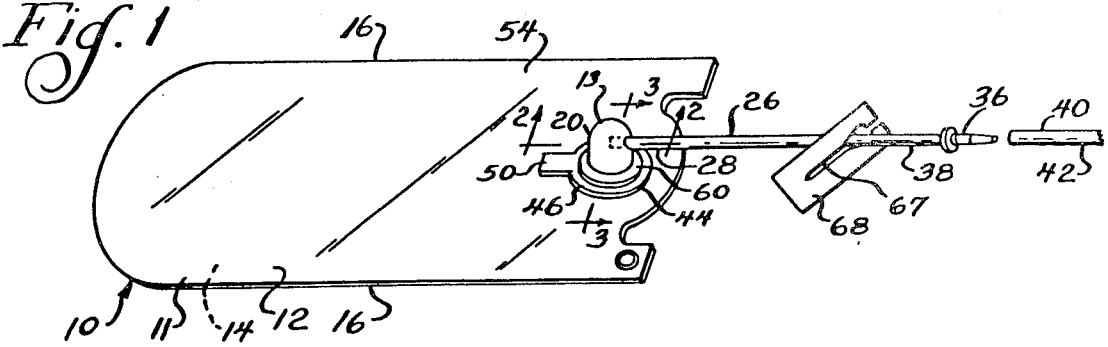
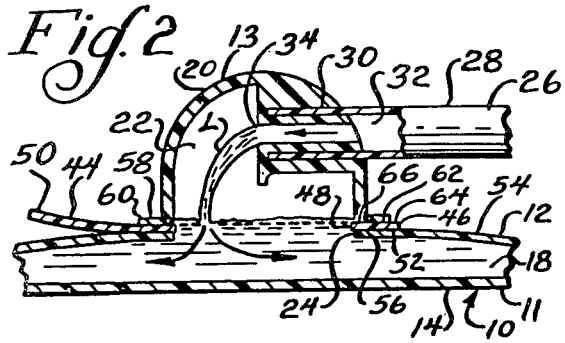
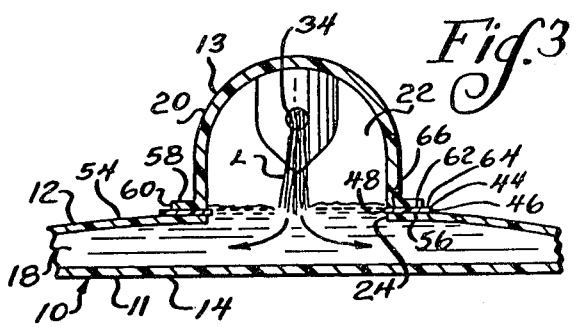
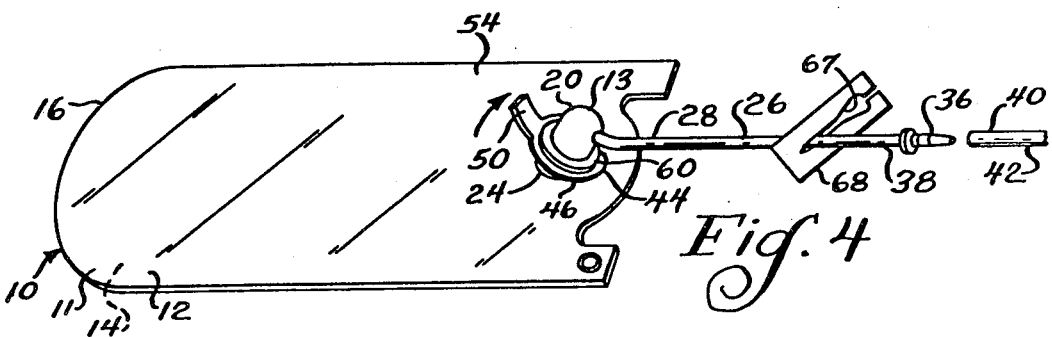
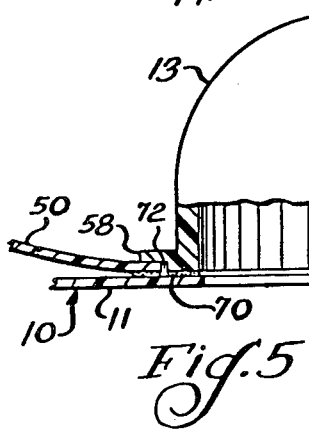
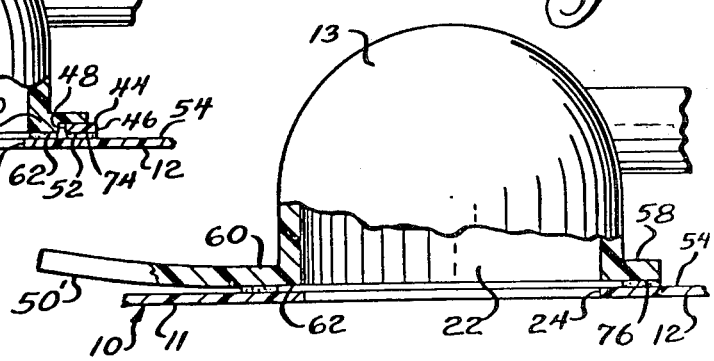

COLLECTION BAG

This application is a division of Ser. No. 137,225, filed Apr. 4, 1980, now U.S. Pat. No. 4,313,447, issued Feb. 2, 1982, which in turn is a continuation-in-part of Ser. No. 004,972 filed Jan. 22, 1979, now abandoned, and which in turn is a continuation of Ser. No. 791,658, filed Apr. 28, 1977, now abandoned.

BACKGROUND OF THE INVENTION

The present invention relates to fluid collection receptacles, and more particularly to collection bags for receiving and collecting body fluids.

In the past, an assortment of receptacles have been proposed to collect body fluids, such as bags which collect urine during catheterization. In the usual form, urine collection receptacles are designed for use throughout an extended period of catheterization, and thus include valves or related devices which may be utilized to empty the bags or obtain samples during catheterization. However, in many instances it is only necessary to catheterize a patient over a relatively short period of time, and the normal bags with valves have been found unnecessarily complex in structure and expensive for this purpose since the short-term bags are discarded after a single use.

Of course, it is desirable that such single-use bags permit access to the collected fluid after catheterization in order to empty the bags prior to disposal or obtain a fluid sample, when required. In the past, tools, such as scissors, have been utilized to sever a corner of the bags in order to open the bag after which the bag contents could be poured through the opening. However, such a procedure has required accessory equipment in the vicinity of the patient, and has been found inconvenient to hospital personnel.

SUMMARY OF THE INVENTION

A principal feature of the present invention is the provision of an improved bag of simplified construction for use in collecting body fluids.

The bag of the present invention comprises, a receptacle having a pair of opposed walls defining a chamber, with one of the walls having an opening communicating with the chamber, and a connector having a cavity to receive the body fluids. The bag also has means for attaching the connector to the one wall over the opening with the connector cavity communicating with the receptacle chamber to permit passage of fluids from the connector into the chamber for collection therein, and for rupturing the connector from the one wall after use of the bag including a tab to permit access to the collected fluid through the opening.

A feature of the present invention is that the bag may be utilized to collect body fluids in the receptacle chamber.

Another feature of the invention is that the tab may be utilized to remove the connector from the receptacle wall and to provide access to the collected fluid in the chamber after use of the bag.

A further feature of the invention is that the collected fluid may be emptied through the wall opening or a sample of the collected fluid may be obtained through the wall opening.

Thus, a feature of the invention is that the collection bag permits access to the fluid contents in a convenient and simplified manner without the necessity of accessory tools.

Further features will become more fully apparent in the following description of the embodiments of this invention and from the appended claims.

DESCRIPTION OF THE DRAWINGS

In the drawings:

FIG. 1 is a perspective view of a collection bag of the present invention;

FIG. 2 is a fragmentary sectional view taken substantially as indicated along the line 2—2 of FIG. 1;

FIG. 3 is a fragmentary sectional view taken substantially as indicated along the line 3—3 of FIG. 1;

FIG. 4 is a perspective view of the bag of FIG. 1 illustrating removal of a connector from a bag wall;

FIG. 5 is a fragmentary elevational view, taken partly in section, of another embodiment of a collection bag of the present invention; and FIG. 6 is a fragmentary elevational view, taken partly in section, of another embodiment of a collection bag of the present invention.

DESCRIPTION OF THE PREFERRED EMBODIMENTS

Referring now to FIGS. 1-3, there is shown a collection or drainage bag generally designated 10 having a receptacle 11 and a connector 13 attached to the receptacle 11. As shown, the receptacle 11 has a pair of opposed front and back walls 12 and 14, respectively, which may be made from a flexible material, such as polyethylene or polyvinyl chloride, and which may be sealed together at their sides 16 in order to define a collection chamber 18 in the receptacle. In a preferred form, the connector 13 comprises a drip chamber having a wall 20 defining an inner cavity 22 which communicates with the receptacle chamber 18 through an opening 24 in only the receptacle front wall 12. Also, the collection bag 10 has a drainage tube 26 having a downstream end 28 received in an annular groove 30 of the connector 13, such that a lumen 32 of the drainage tube 26 communicates with the connector cavity 22 through an inlet port 34 of the connector 13.

During catheterization, an adapter 36 at an upstream end 38 of the drainage tube 26 is connected to a proximal end 40 of a catheter 42. Thus, urine L drains through the catheter 42 and drainage tube 26 into the connector cavity 22 after which it passes from the connector 13 into the receptacle chamber 18 for collection therein. The drainage system and receptacle are closed to the atmosphere in order to maintain the system in a sterile condition, and, as will be seen below, the drainage bag of the present invention permits ready access to the fluid contents of the closed bag after catheterization has been completed.

Thus, with reference to FIGS. 1-3, the bag 10 has a rupture member 44 of flexible material, such as polyethylene or polyvinyl chloride, comprising a ring 46 having an opening 48 of a size similar to the size of the wall opening 24, and having an integral free tab 50 extending outwardly from the ring 46 relative the wall opening 24. A lower surface 52 of the ring 46 is attached to an outer surface 54 of the front wall 12 in a region of bonding 56 which extends peripherally around the front wall opening 24. The ring 46 of the rupture member 44 is fixedly bonded to the wall 12 with sufficient strength to prevent reattachment to the wall 12 after being ruptured therefrom. Also, the connector 13 has a lower outwardly directed flange 58 defining a connector base 60 having a lower generally planar surface 62. As shown, the lower surface 62 of the connector base 60 is fixedly attached to an outer surface 64 of the ring 46 in a region of bonding 66 which extends peripherally around the receptacle opening 24 and rupture member opening 48. In a suitable form, the bonding regions 56 and 66 may be defined by adhesive or by heat sealing between the components. Thus, the connector 13 is attached to the receptacle front wall 12 by bonding between the connector base 60 and the rupture member 44 in the region 66 and by bonding between the rupture member 44 and the receptacle front wall 12 in the region 56.

During catheterization, the back wall 14 of the receptacle 11 normally rests upon a support surface, such that the connector 13 is located above the receptacle. The drainage tube 26 may be selectively opened or closed by a shaped slot 67 in a suitable clamp 68 during or after catheterization. Thus, after catheterization has been completed, the drainage tube 26 may be closed by the clamp 68, and the adapter 36 of the drainage tube 26 may be removed from the catheter 42.

At this time, with reference to FIG. 4, the tab 50 of the rupture member 44 may be grasped by the attendant, such as a nurse, and pulled in a direction away from the receptacle front wall 12 as indicated by the direction of the arrow in the drawing, in order to rupture or sever the bonding region 56 between the rupture member ring 46 and the front wall 12. In this manner, the connector 13 may be readily removed from the receptacle front 12 only once in order to provide access to the collected urine through the wall opening 24 after catheterization has been completed. Of course, the connector 13 is attached with sufficient strength to maintain the connector on the receptacle during catheterization and prevent premature release of the connector from the receptacle. After the connector 13 has been removed from the receptacle 11, the fluid contents may be emptied through the receptacle opening 24, or a urine sample may be obtained through the opening 24, if desired. Thus, in accordance with the present invention, the collection bag may be used for a single catheterization after which the collected fluid may be removed from the receptacle chamber in a convenient and simplified manner without the requirement of accessory tools, such as scissors, which would be otherwise necessary to sever the bag.

Another embodiment of the present invention is illustrated in FIG. 5, in which like reference numerals designate like parts. In this embodiment, the attachment such as adhesive directly bonds the lower surface 62 of an inner base portion to the outer wall surface 54 in a bonding region 70 which extends peripherally around the receptacle opening 24. The base is fixedly bonded to the wall 12 with sufficient strength to prevent reattachment to the wall 12 after being ruptured therefrom. As before, the rupture member 44 comprises a ring 46 and a free tab 50 which extends outwardly from the ring 46 relative the receptacle opening 24. However, in this embodiment, the ring opening 48 is spaced from the receptacle opening 24, such that the bonded portion of the connector base 60 is located intermediate the ring 46 and the receptacle opening 24. In a preferred form, the flange 58 of the connector base 60 has an annular recess 72 at a lower outer portion of the base 60 to receive the rupture member ring 46 intermediate the flange 58 and the outer surface 54 of the front wall 12. Also, in a preferred form, the lower surface 52 of the ring 46 is bonded to the outer surface 54 of the front wall 12 by suitable means, such as adhesive, in a bonding region 74 which extends peripherally around the outside of the bonding region 70 between the connector base 60 and the receptacle 11.

In this manner, the connector 13 is directly bonded to the receptacle front wall 12, and the rupture member 44 is received intermediate an outer portion of the connector base 60 and the receptacle front wall 12. After catheterization has been completed, the tab 50 of the rupture member 44 may be grasped and pulled in order to rupture the ring 46 and the connector 13 from the receptacle front wall 12 only once in a manner as previously described.

Another embodiment of the present invention is illustrated in FIG. 6, in which like reference numerals designate like parts. In this embodiment, the lower surface 62 of the connector base 60 is directly bonded to the outer surface 54 of the receptacle front wall 12 by suitable means, such as adhesive or heat sealing, in a bonding region 76 which extends peripherally around the receptacle opening 24. The base is fixedly bonded to the wall 12 with sufficient strength to prevent reattachment to the wall 12 after being ruptured therefrom. Also, in this embodiment, the free tab 50' comprises an integral portion of the connector flange 58 and extends outwardly from a lower portion of the connector 13 adjacent the base 60. Thus, after catheterization has been completed, the tab 50' may be grasped by the attendant and pulled in order to rupture the bonding region 76 between the connector 13 and the receptacle front wall 12. In this manner, the connector 13 is removed from the receptacle 11 only once in order to provide access to the collected fluid through the receptacle opening 24. In a preferred form, the connector 13 may be made from a flexible material, such as polyethylene or polyvinyl chloride, in order that the tab 50' is relatively flexible and may be readily grasped during removal of the connector 13 from the receptacle 11.

The foregoing detailed description is given for clearness of understanding only, and no unnecessary limitations should be understood therefrom, as modifications will be obvious to those skilled in the art.

We claim:

1. A collection bag for receiving and collecting body fluids, comprising:

a receptacle having a pair of opposed walls defining a chamber, means defining an opening through only one of said walls, the wall opening means communicating with the chamber, and means defining a region of bonding which extends peripherally about the wall opening means;

a connector having a cavity to receive the body fluids and opening means defined through said connector having dimensions substantially the same as those of said wall opening means, there being a peripheral flange extending outwardly from said connector opening means to define a base having a lower planar surface with an inner circumference substantially the same as that of said wall opening means region of bonding;

a rupture member in the form of a ring having a lower surface and an outer, upper surface, said ring having an inner circumference substantially the same as those of said wall and connector opening means, bonding means for affixing said ring lower surface to said wall opening means region of bonding with sufficient strength to prevent reattachment to the one wall opening means region of bonding after being ruptured therefrom, additional bonding means for affixing said ring outer upper surface to said connector upper flange, said ring and connector remaining in assembly subsequent to rupturing of said rupture member from said receptacle one wall, and a tab extending outwardly from the ring and graspable by the fingers of a user to move said tab upwardly from said receptacle one wall, thus to rupture said rupture member and connector unitary assembly from said receptacle one wall; and a conduit extending from the connector and communication with said connector cavity.

* * * * *